United States Patent [19]

Schmidt et al.

[11] 4,396,767

[45] Aug. 2, 1983

[54] 2,6-BIS(HETEROARYL)PYRIDINES

[75] Inventors: Paul J. Schmidt, Sharonville; William M. Hung, Cincinnati, both of Ohio

[73] Assignee: Sterling Drug Inc., New York, N.Y.

[21] Appl. No.: 244,490

[22] Filed: Mar. 16, 1981

[51] Int. Cl.$^3$ .................................. C07D 455/04
[52] U.S. Cl. .................................. 546/94; 546/256; 546/272; 546/273; 546/281; 544/124; 427/151; 428/411; 282/27.5
[58] Field of Search .................. 546/256, 272, 94

[56] References Cited

U.S. PATENT DOCUMENTS 3,985,376 10/1976 Baumann et al. .................. 282/27.5
4,032,527 6/1977 Crounse et al. .................. 546/94
4,140,689 2/1979 Foley et al. .................. 546/94

OTHER PUBLICATIONS

M. Weiss, J. Amer. Chem. Soc. 74, 200–202, (1952).
E. Koenigs et al., Ann. 509, 142–158, (1934).

*Primary Examiner*—Alan L. Rotman
*Attorney, Agent, or Firm*—Paul E. Dupont; B. Woodrow Wyatt

[57] ABSTRACT

Novel 4-[4-(substituted-amino)phenyl]- or heteroaryl-2,6-bis(heteroaryl)pyridines which are useful as color formers in pressure-sensitive carbonless duplicating systems and thermal marking systems are prepared by reacting a heteroaryl methyl ketone with a 2-$R_4$-4-$NR_5R_6$-benzaldehyde or a heteroaryl aldehyde in the presence of ammonia or an ammonia-releasing agent.

2 Claims, No Drawings

2,6-BIS(HETEROARYL)PYRIDINES

BACKGROUND OF THE INVENTION

1. Field of the Invention

This invention relates to a group of compounds classified in the field of organic chemistry as 4-[4-(substituted-amino)phenyl]- or heteroaryl-2,6-bis(heteroaryl)-pyridines useful as color formers in pressure-sensitive carbonless duplicating systems and thermal marking systems, to a process for the preparation thereof and to pressure-sensitive carbonless duplicating systems and thermal marking systems containing the same.

2. Description of the Prior Art

Several classes of organic compounds of widely diverse structural types are known to be useful as color formers for carbonless duplicating systems. Among the more important classes are the phenothiazines, for example N-benzoyl leuco methylene blue; fluorans, for example 2'-anilino-6'-diethylaminofluoran; phthalides, for example crystal violet lactone; arylsulfinate salts of Michler's Hydrol; substituted phenylpyridines and various other types of colorless precursors currently employed in commercially accepted carbonless copy systems. Typical of the many such systems taught in the prior art are those described in U.S. Pat. Nos. 2,712,507, 2,800,457, 3,041,289 and 4,000,087, which issued July 5, 1955, July 23, 1957, June 26, 1962 and Dec. 28, 1976, respectively. Many of the color formers in the prior art suffer one or more disadvantages such as low tinctorial strength, poor light stability, poor xerographic copiability and low solubility in common organic solvents, the latter disadvantage thus requiring the use of specialized and expensive solvents in order to obtain microencapsulated solutions of sufficient concentration for use in pressure-sensitive copy systems.

The following appear to constitute the most pertinent prior art relative to the present invention.

Baumann et al., U.S. Pat. No. 3,985,376, patented Oct. 12, 1976 discloses compounds of the formula

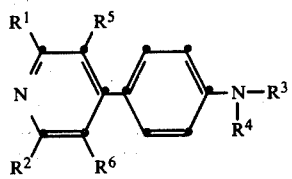

in which
R¹ and R² are hydrogen or alkyl or aryl of one to eight carbon atoms which may bear alkoxy or halogen as a substituent;
R³ is hydrogen or alkyl of one to five carbon atoms;
R⁴ is alkyl, haloalkyl, cyanalkyl, aryl or aralkyl of one to eight carbon atoms which may bear alkoxy as a substituent;
R⁵ and R⁶ are hydrogen or carbalkoxy of two to five carbon atoms and R³ and R⁴ may be closed to form a ring. Specific compounds disclosed are those wherein R¹ and R² are each phenyl, R⁵ and R⁶ are each hydrogen, R³ is methyl and R⁴ is methyl, phenyl or p-ethoxyphenyl, and also those wherein R¹ and R² are each p-methoxyphenyl, R⁵ and R⁶ are each hydrogen and R³ and R⁴ are each methyl. The compounds are stated to be useful as dye precursors for pressure-sensitive recording material.

M. Weiss, J. Amer. Chem. Soc. 74, 200–202 (1952) discloses in most pertinent part compounds of the formula

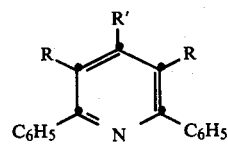

wherein R is hydrogen and R' is phenyl, 4-methoxyphenyl, 3,4-methylenedioxyphenyl, 4-dimethylaminophenyl or 2-methoxyphenyl. These compounds were isolated as reaction products in a study of the Chichibabin synthesis.

E. Koenigs and E. Ruppelt, Ann. 509, 142–158 (1934) disclose as basic dyestuffs a number of 4-[p-dialkylaminophenyl]-pyridines.

3. Prior Publications

The following United Kingdom Patent Application was published prior to the filing of applicants' instant application but subsequent to the completion of applicants' invention.

United Kingdom Patent Application No. 2,029,591A pusblished Mar. 19, 1980 discloses pyridine derivatives having the formula

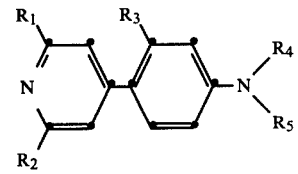

wherein
R₁ and R₂ are independently hydrogen, phenyl group or chlorine-substituted phenyl groups;
R₃ is hydrogen, lower-alkyl groups or lower-alkoxy groups;
R₄ and R₅ are independently lower-alkyl groups, benzyl group or phenyl group, said lower-alkyl groups possibly being substituted with a cyano group, a chlorine atom or a lower-alkoxy group. The compounds are stated to produce a yellow color on heating in the presence of an electron acceptor.

SUMMARY OF THE INVENTION

The present invention provides novel 4-[4-(substituted-amino)phenyl]- or heteroaryl-2,6-bis(heteroalkyl)-pyridines useful as color formers in pressure-sensitive carbonless duplicating systems and thermal marking systems. The compounds develop light-stable colored images of good tinctorial strength and are soluble in common organic solvents. Moreover, because the compounds produce yellow to orange colors they are especially valuable as toners used in admixture with other color formers to produce images of a neutral shade. The invention also provides a process for the preparation of these compounds as well as pressure-sensitive carbonless duplicating systems and thermal marking systems containing them.

In a composition of matter aspect the invention relates to a series of 4-(2-R₄-4-NR₅R₆-phenyl)- or heteroaryl-2,6-bis(heteroaryl)pyridines which are useful as color formers in pressure-sensitive carbonless duplicating systems and thermal marking systems.

In a process aspect the present invention provides a process for preparing 4-(2-$R_4$-4-$NR_5R_6$-phenyl)- or heteroaryl-2,6-bis(heteroalkyl)pyridines which comprises reacting a heteroaryl methyl ketone with a 2-$R_4$-4-$NR_5R_6$-benzaldehyde or a heteroaryl aldehyde in the presence of ammonia or an ammonia-releasing agent.

In an article of manufacture aspect the present invention relates to a pressure-sensitive carbonless duplicating system or thermal marking system containing a color-forming substance comprising at least one of the 4-(2-$R_4$-4-$NR_5R_6$-phenyl)- or heteroaryl-2,6-bis(heteroaryl)pyridines of the invention.

DETAILED DESCRIPTION OF THE INVENTION INCLUSIVE OF THE PREFERRED EMBODIMENTS

In a composition of matter aspect the invention sought to be patented resides in a compound having Formula I hereinbelow:

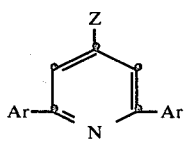

Formula I wherein:
Ar is a substituent having the formula

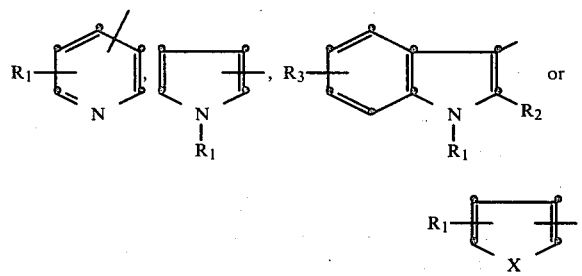

in which:
$R_1$ is hydrogen or non-tertiary lower-alkyl;
$R_2$ is hydrogen, phenyl or non-tertiary lower-alkyl;
$R_3$ is hydrogen, non-tertiary lower-alkyl or non-tertiary lower-alkoxy;
X is O or S;
Z is 9-julolidinyl or a substituent having the formula

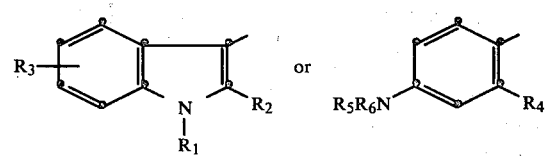

in which:
$R_4$ is hydrogen, lower-alkyl, halo, lower-alkoxy, lower-alkoxycarbonyl or di-lower-alkylamino;
$R_5$ is lower-alkyl, and
$R_6$ is lower-alkyl, benzyl, cyano-lower-alkyl, or
$NR_5R_6$ is pyrrolidinyl, piperidinyl, morpholinyl or isoindolinyl.

These compounds are useful as color formers for pressure-sensitive carbonless duplicating systems and thermal marking systems.

A particular embodiment sought to be patented resides in a compound having Formula I hereinabove wherein Ar is a substituent having the formula

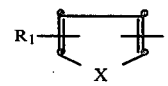

and Z is a substituent having the formula

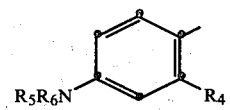

Preferred compounds with the ambit of this embodiment are those wherein $R_1$ and X have the previously given meanings, $R_4$ is hydrogen or halo and $R_5$ and $R_6$ are each lower-alkyl, especially 4-[4-(dimethylamino)-phenyl]-2,6-bis(2-thienyl)pyridine, 4-[4-(dimethylamino)phenyl]-2,6-bis(2-furyl)pyridine and 4-[2-chloro-4-(dimethylamino)phenyl]-2,6-bis(2-thienyl)-pyridine. These compounds are particularly valuable because they are easily prepared from inexpensive and readily available starting materials.

In its process aspect the invention sought to be patented resides in a process for preparing the compounds of Formula I hereinabove which comprises reacting approximately two molar equivalents of a heteroaryl methyl ketone having Formula II hereinbelow:

Ar—COCH$_3$ 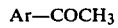 Formula II with approximately one molar equivalent of an aryl or heteroaryl aldehyde having Formula III hereinbelow:

Z—CHO  Formula III in the presence of ammonia or an ammonia-releasing agent where in Formulas II and III Ar and Z have the previously given meanings.

In an article of manufacture aspect, the invention sought to be patented resides in a pressure-sensitive carbonless duplicating system or thermal marking system containing a support sheet coated with a color-forming substance comprising a compound having Formula I hereinabove.

A particular embodiment sought to be patented resides in a pressure-sensitive transfer sheet adapted for use with a receiving sheet having an electronic accepting layer comprising a support sheet coated on one side with a layer of pressure-rupturable microcapsules, said microcapsules containing a liquid solution of a color-forming substance comprising at least one compound having Formula I.

Another particular embodiment sought to be patented resides in a heat-responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

A further embodiment sought to be patented resides in a pressure-sensitive carbonless duplicating system or a thermal marking system containing a support sheet coated with a color-forming substance comprising a compound having Formula I hereinabove in combination with a blue or green and a red or orange color-former.

Preferred articles within the ambit of the particular embodiments above-described are those having a color-forming component of Formula I hereinabove in which Z is a substituent having the formula

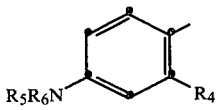

especially where $R_4$ is hydrogen or halo and $R_5$ and $R_6$ are each lower-alkyl, and where Ar in Formula I is a substituent having the formula

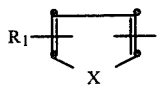

$R_1$ and X having the previously given meanings.

As used herein the term "halo" includes fluoro, chloro, bromo and iodo.

In the terms "lower-alkyl," "cyano-lower-alkyl", "lower-alkoxy", "lower-alkoxycarbonyl" and "di-lower-alkylamino", "lower-" denotes a saturated acyclic alkyl moiety having 1 to 4 carbon atoms such as methyl, ethyl, propyl, isopropyl, butyl, sec-butyl or isobutyl.

The terms "isoindolinyl" and "9-julolidinyl," of course, refer respectively to the radicals having the formulas

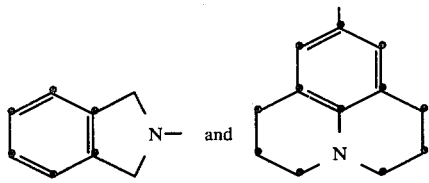

In accordance with the process aspect of this invention the compounds having Formula I hereinabove are obtained by reacting approximately two molar equivalents of a heteroaryl methyl ketone of Formula II hereinabove with approximately one molar equivalent of an aryl or heteroaryl aldehyde of Formula III hereinabove in the presence of ammonia or an ammonia-releasing agent. Thus, the ketone and aldehyde can be condensed in the presence of aqueous or alcoholic ammonia or alternatively, and preferably, in the presence of an ammonia-releasing agent such as ammonium acetate in acetic acid. The reactants are heated at about 50°–150° C. for approximately 1 to 5 hours, usually at the reflux temperature of the solvent for about 2 hours. The product thus obtained can be isolated by filtration if it is insoluble in the reaction medium, or by dilution of the reaction medium with a miscible solvent in which the product is insoluble such as water or a lower-alkanol, for example, isopropyl alcohol, or a mixture of these in order to effect precipitation of the product. Alternatively, the reaction mixture can be poured into water or dilute ammonium hydroxide and the product extracted with an organic solvent such as benzene, toluene or chloroform followed by evaporation of the organic solvent leaving the product as a residue. Frequently the product begins to separate from the reaction mixture as an oil. Usually the addition of a lower-alkanol such as ethanol or isopropyl alcohol to the hot reaction mixture will induce the product to separate in crystalline form on cooling. The product once isolated can be purified by conventional means such as trituration or recrystallization from a suitable solvent.

The heteroaryl methyl ketones of Formula II and the aryl or heteroaryl aldehydes of Formula III which are required as starting materials in the preparation of the final products of Formula I are generally known and are either commercially available or readily obtained by conventional procedures well known in the art. Those ketones and aldehydes which are specifically novel can be prepared in accordance with the procedures described for preparation of the known compounds.

The novel compounds of Formula I hereinabove are pale yellow to colorless in the depicted form. When contacted with an acidic medium, for example silica gel, or one of the types ordinarily employed in pressure-sensitive carbonless duplicating systems such as silton clay or phenolic resins, the compounds of Formula I develop an intense yellow to orange image which is xerographically reproducible and light stable. The compounds are thus highly suitable for use as color precursors, that is, color-forming substances in pressure-sensitive carbonless duplicating systems. Because they produce a yellow to orange color, these compounds are especially valuable as toners which are used in admixture with other color formers to produce images of a neutral shade which desirably possess excellent xerographic reproducibility. Thus, a yellow to orange color former of Formula I hereinabove can be combined with a red or orange color former and a blue or green color former to afford a color-forming substance which produces a neutral or black image.

The compounds of this invention may be incorporated in any of the commercially accepted systems known in the cabonless duplicating art. A typical technique for such application is as follows: solutions containing one or more color precursor compounds of Formula I optionally in admixture with other color formers as noted above in suitable solvents are microencapsulated by well-known procedures, for example as described in U.S. Pat. Nos. 3,649,649, 3,429,827 and 4,000,087. The microcapsules are coated on the reverse side of a transfer sheet with the aid of a suitable binder and the coated transfer sheet is then assembled in a manifold with the microcapsule-coated side in contact with a receiving sheet coated with an electron accepting substance for example silton clay or phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms a colored image. It is, of course, obvious that variants of this mode of application can be utilized. For example, the receiving sheet in a manifold can alternatively be coated with the subject compounds and the acidic developing agent can be contained in microcapsules applied on the reverse side of the top sheet in the manifold, or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. Nos. 3,447,944 and 3,539,375, that is, papers which produce a colored image when contacted with a heated stylus or heated type, for example bisphenol A, heating of the mixture produces a colored image of varying shades from yellow to orange depending on the particular compound of the invention employed. As noted above, darker shades can be produced by mixing the compounds of Formula I with other color formers. The ability of the compounds of Formula I to form an intense color when heated in admixture with an acidic developer such as bisphenol A makes them useful in thermal paper marking systems either where an original or duplicate copy is prepared by contacting the thermal paper with a heated stylus or heated type in any of the methods generally known in the art.

The molecular structure of the compounds of this invention were assigned on the basis of the modes of synthesis, elemental analysis and study of their infrared and nuclear magnetic resonance spectra.

The following examples will further illustrate the invention without however limiting it thereto.

EXAMPLE 1

A mixture containing 7.5 g. of 4-(dimethylamino)-benzaldehyde, 11 g. of 2-acetylfuran, 50 g. of ammonium acetate and 60 ml. of glacial acetic acid was refluxed for two hours. After cooling to room temperature, the reaction mixture was quenched with water and extracted with toluene. The toluene layer was separated, washed successively with water and saturated aqueous sodium chloride, and evaporated to dryness under vacuum. The residue was triturated with isopropanolhexane to give 2.3 g. of 4-[4-(diethylamino)-phenyl]-2,6-bis(2-furyl)pyridine, as a tan solid, m.p. 124°–125° C. A toluene solution of the product developed an orange image when contacted with acidic clay and a yellow image when contacted with phenolic resin.

EXAMPLE 2

A mixture containing 9.2 g. of 2-chloro-4-(dimethylamino)benzaldehyde, 13 g. of 2-acetylthiophene, 50 g. of ammonium acetate and 60 ml. of glacial acetic acid was heated under reflux 1.5 hours. The reaction mixture was cooled and the liquid was decanted. The tarry residue was broken up and slurried with 75 ml. of acetone. The solid was collected by filtration, reslurried in 100 ml. of acetone and filtered to give 2.9 g. of 4-[2-chloro-4-(dimethylamino)phenyl]-2,6-bis(2-thienyl)-pyridine, as a yellow solid, m.p. 147°–150° C. This product produced a yellow image on contact with acidic clay or phenolic resin.

EXAMPLE 3

Following a procedure similar to that described in Example 1 but employing 7.5 g. of 4-(dimethylamino)-benzaldehyde, 12.7 g. of 2-acetylthiophene, 50 g. of ammonium acetate and 60 ml. of glacial acetic acid there was obtained 2.8 g. of 4-[4-(dimethylamino)-phenyl]-2,6-bis(2-thienyl)pyridine as a yellow solid, m.p. 90°–97° C. This product produced a yellow image on contact with acidic clay or phenolic resin.

EXAMPLE 4

A mixture containing 6.0 g. of 4-(dimethylamino)-benzaldehyde, 10 g. of 2-acetyl-1-methylpyrrole, 50 g. of ammonium acetate and 60 ml. of glacial acetic acid was heated 2 hours under reflux. After cooling to room temperature, 50 ml. of isopropanol was added and the resulting mixture was heated 1 hour under reflux. After cooling, the solid was collected by filtration, slurried in 100 ml. of isopropanol, and filtered to give 3.6 g. of 4-[4-(dimethylamino)phenyl]-2,6-bis(1-methylpyrrol-2-yl)pyridine, as a straw-yellow solid. This product produced a yellow image on contact with acidic clay or phenolic resin.

EXAMPLE 5

Following a procedure similar to that described in Example 1 but employing 7.5 g. of 4-[(2-cyanoethyl)methylamino]-benzaldehyde, 9.8 g. of 2-acetylthiophene, 53 g. of ammonium acetate and 40 ml. of glacial acetic acid there was obtained 4.6 g. of 4-[4-[(2-cyanoethyl)-methylamino]phenyl]-2,6-bis(2-thienyl)pyridine as a brownish-yellow solid, m.p. 94°–110° C. This product produced a yellow image on contact with acidic clay or phenolic resin.

EXAMPLE 6

Following a procedure similar to that described in Example 1 but employing 7.5 g. of 4-(dimethylamino)-benzaldehyde, 12.2 g. of 4-acetylpyridine, 50 g. of ammonium acetate and 60 ml. of glacial acetic acid there was obtained 6.4 g. of 4-[4-(dimethylamino)phenyl]-2,6-bis(4-pyridinyl)pyridine, as a yellow solid, m.p. 224°–226° C. This product produced a yellow image on contact with acidic clay or phenolic resin.

EXAMPLE 7

Following a procedure similar to that described in Example 1 but employing 4.7 g. of 2,4-bis(dimethylamino)-benzaldehyde, 6.0 g. of 2-acetylthiophene, 32 g. of ammonium acetate and 20 ml. of glacial acetic acid there was obtained 0.6 g. of 4-[2,4-bis(dimethylamino)phenyl]-2,6-bis(2-thienyl)pyridine, as a brown solid, m.p. 73°–100° C. This product produced an orange image on contact with acidic clay or phenolic resin.

EXAMPLE 8

Following a procedure similar to that described in Example 1 but employing 8.8 g. of 2-ethoxy-4-(diethylamino)benzaldehyde, 10.1 g. of 2-acetylthiophene, 52 g. of ammonium acetate and 30 ml. of glacial acetic acid there was obtained 0.6 g. of 4-[2-ethoxy-4-(diethylamino)phenyl]-2,6-bis(2-thienyl)-pyridine, as a yellow brown solid, m.p. 91°–104° C. This product produced a yellow image on contact with acidic clay or phenolic resin.

EXAMPLE 9

Following a procedure similar to that described in Example 1 but employing 5.3 g. of the ethyl ester of 2-formyl-5-(dimethylamino)benzoic acid, 5.8 g. of 4-acetylpyridine, 30 g. of ammonium acetate and 25 ml. of glacial acetic acid there was obtained 0.8 g. of 4-[2-(ethoxycarbonyl)-4-(dimethylamino)-phenyl]2,6-bis(4-pyridinyl)pyridine as a light yellow solid, m.p.

205°–215° C. This product produced a yellow image on contact with acidic clay or phenolic resin.

EXAMPLE 10

Following a procedure similar to that described in Example 1 but employing 2.5 g. of 4-(dimethylamino)-benzaldehyde, 6.2 g. of 3-acetyl-2-methylindole, 30 g. of ammonium acetate and 20 ml. of glacial acetic acid there was obtained 0.8 g. of 4-[4-(dimethylamino)-phenyl]-2,6-bis(2-methylindol-3-yl)-pyridine, as a yellow solid, m.p. 171°–176° C. This product produced a yellow image on contact with acidic clay or phenolic resin.

EXAMPLE 11

Following a procedure similar to that described in Example 4 but employing 6.1 g. of 9-julolidinecarboxaldehyde, 7.6 g. of 2-acetylthiophene, 40 g. of ammonium acetate and 30 ml. of glacial acetic acid there was obtained 4.8 g. of 4-(9-julolidinyl)-2,6-bis(2-thienyl)-pyridine, as an orange solid, m.p. 198°–203° C. This product produced a pinkish yellow image on contact with acidic clay or phenolic resin.

EXAMPLE 12

A mixture containing 5.6 g. of 4-isoindolinylbenzaldehyde, 6.5 g. of 2-acetylthiophene, 30 g. of ammonium acetate and 40 ml. of glacial acetic acid was refluxed for two hours. After cooling to room temperature, the solid was collected by filtration and washed with water. The solid was then slurried in 150 ml. of ethanol, collected by filtration, and washed successively with 50 ml. portions of ethanol and acetone to give 4.2 g. of 4-(4-isoindolinylphenyl)-2,6-bis(2-thienyl)pyridine, as a muddy yellow solid, m.p. 185°–188° C. This product produced a yellow image on contact with acidic clay or phenolic resin.

EXAMPLE 13

Following a procedure similar to that described in Example 1 but employing 4.8 g. of 2-methyl-4-(1-pyrrolidinyl)-benzaldehyde, 6.5 g. of 2-acetylthiophene, 40 g. of ammonium acetate and 50 ml. of glacial acetic acid there was obtained 1.1 g. of 4-[2-methyl-4-(1-pyrrolidinyl)phenyl]-2,6-bis(2-thienyl)pyridine as a tan solid, m.p. 75°–85° C. This product produced an orange image on contact with acidic clay or phenolic resin.

EXAMPLE 14

Following a procedure similar to that described in Example 1 but employing 9.5 g. of 4-(1-piperidinyl)benzaldehyde, 13 g. of 2-acetylthiophene, 50 g. of ammonium acetate and 60 ml. of glacial acetic acid there was obtained 3.7 g. of 4-[4-(1-piperidinyl)phenyl]-2,6-bis(2-thienyl)pyridine, as a yellow solid, m.p. 146°–149° C. This product produced a yellow image on contact with acidic clay or phenolic resin.

EXAMPLE 15

Following a procedure similar to that described in Example 4 but employing 6.7 g. of 4-(4-morpholinyl)-benzaldehyde, 8.3 g. of 2-acetylthiophene, 50 g. of ammonium acetate and 60 ml. of glacial acetic acid there was obtained 1.8 g. of 4-[4-(4-morpholinyl)phenyl]-2,6-bis(2-thienyl)pyridine, as a yellow solid, m.p. 161°–166° C. This product produced a yellow image on contact with acidic clay or phenolic resin.

EXAMPLE 16

Following a procedure similar to that described in Example 1 but employing 5.6 g. of 1-ethyl-2-methylindole-3-carboxaldehyde, 6.6 g. of 2-acetylfuran, 40 g. of ammonium acetate and 30 ml. of glacial acetic acid there was obtained 1 g. of 4-(1-ethyl-2-methylindol-3-yl)-2,6-bis(2-furyl)pyridine, m.p. 145°–150.5° C. This product developed a brownish-yellow image on contact with acidic clay or phenolic resin.

EXAMPLE 17

Following a procedure similar to that described in Example 1 but employing 7.2 g. of 4-(benzylethylamino(benzaldehyde, 7.3 g. of 4-acetylpyridine, 40 g. of ammonium acetate and 25 ml. of glacial acetic acid there was obtained 3.7 g. of 4-[4-(benzylethylamino(-phenyl]-2,6-bis(4-pyridyl)pyridine, m.p. 210°–213° C. This product developed a yellow image on contact with acidic clay or phenolic resin.

It is contemplated that by following procedures similar to those described in Examples 1, 2, 4 and 12 but employing the appropriately substituted heteroaryl methyl ketones and aryl or heteroaryl aldehydes of Formulas II and III, respectively, there will be obtained the 4-[4-(substituted-amino)phenyl] or heteroaryl-2,6-bis(heteroaryl)pyridines of Formula I, Examples 18–29 presented in Table A hereinbelow.

TABLE A

| Ex. | Ar | Z |
|---|---|---|
| 18 | 5-$CH_3$—2-furyl | 4-$(CH_3)_2$N—$C_6H_4$ |
| 19 | 5-$CH_3$—2-thienyl | 4-$(CH_3)_2$N—$C_6H_4$ |
| 20 | 2,4-$(CH_3)_2$—2-pyrrolyl | 4-$(CH_3)_2$N—$C_6H_4$ |
| 21 | 2-pyridinyl | 4-$(CH_3)_2$N—$C_6H_4$ |
| 22 | 3-pyridinyl | 4-$(CH_3)_2$N—$C_6H_4$ |
| 23 | 1-$C_2H_5$—2-$CH_3$—3-indolyl | 4-$(C_2H_5)_2$N—$C_6H_4$ |
| 24 | 1-$C_4H_9$—3-indolyl | 4-$(CH_3)_2$N—$C_6H_4$ |
| 25 | 5-$C_4H_9$—2-furyl | 4-$(C_2H_5CH_3N)$—$C_6H_4$ |
| 26 | 5-$C_4H_9$—2-thienyl | 4-$(CH_3)_2$N—$C_6H_4$ |
| 27 | 5-$CH_3O$—1,2-$(CH_3)_2$—3-indolyl | 4-$(CH_3)_2$N—$C_6H_4$ |
| 28 | 2-thienyl | 1-$C_4H_9$—3-indolyl |
| 29 | 2-furyl | 1,2,5-$(CH_3)_3$—3-indolyl |

EXAMPLE 30

A solution containing 0.73 g. of the color former of Example 14 in 30 g. of isopropylbiphenyl and a solution containing 2.5 g. of carboxymethylcellulose in 100 ml. of water were mixed and emulsified by rapid stirring. The desired particle size (1–4 microns) was checked by microscope. To the emulsion was added a solution containing 7.5 g. of pigskin gelatin in 60 ml. of water. The pH was adjusted to 6.5 with 10% aqueous sodium hydroxide with rapid stirring, and following the gradual addition of 335 ml. of water at 50° C. the pH was adjusted to 4.5 with 10% aqueous acetic acid with continued rapid stirring. After 5 minutes, the mixture was cooled to 15° C., treated with 10 g. of 25% aqueous glutaraldehyde and rapidly stirred for 15 minutes. The resulting microcapsule dispersion was stirred more slowly overnight, diluted with water to 560 g. and coated on white typewriter paper sheets. The sheets were air-dried. Duplicated typewritten images were made on receiving sheets coated with either phenolic resin or acidic clay. The color former of Example 14 produced a yellow image on both types of receiving sheets.

EXAMPLE 31

A polyvinyl alcohol dispersion of the color former of Example 1 was prepared by shaking one hour on a paint shaker a mixture containing 2.0 g. of the color former, 3.7 g. of water, 8.6 g. of 10% aqueous polyvinyl alcohol and 10 ml. of zirconium grinding beads. A polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied to white mimeo paper sheets and the sheets were dried at room temperature. Contacting the coated sheets with a heated stylus at a temperature between 100° C. and 150° C. produced a yellow image.

We claim:

1. A compound having the formula

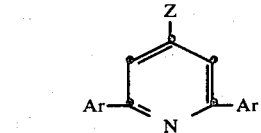

wherein:
Ar is a substitutent having the formula

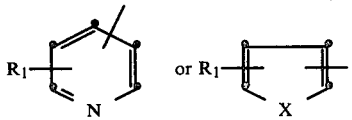

in which:
$R_1$ is hydrogen or non-tertiary lower-alkyl;
X is O or S;
Z is 9-julolidinyl.

2. A compound according to claim 1 wherein Ar is a substituent having the formula

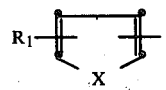

wherein $R_1$ is hydrogen or non-tertiary lower-alkyl and X is O or S.

* * * * *